(12) United States Patent
Muller

(10) Patent No.: US 8,709,012 B2
(45) Date of Patent: Apr. 29, 2014

(54) SURGICAL CUTTING TOOL

(76) Inventor: Erich Johann Muller, Kleinwallstadt (DE)

( * ) Notice: Subject to any disclaimer, the term of this patent is extended or adjusted under 35 U.S.C. 154(b) by 1094 days.

(21) Appl. No.: 12/096,370

(22) PCT Filed: Dec. 5, 2006

(86) PCT No.: PCT/DE2006/002160
§ 371 (c)(1),
(2), (4) Date: Jun. 5, 2008

(87) PCT Pub. No.: WO2007/065419
PCT Pub. Date: Jun. 14, 2007

(65) Prior Publication Data
US 2008/0306482 A1    Dec. 11, 2008

(30) Foreign Application Priority Data
Dec. 5, 2005  (DE) .......................... 10 2005 058 107

(51) Int. Cl.
*A61B 17/00*       (2006.01)
(52) U.S. Cl.
USPC ........................................................... 606/79

(58) Field of Classification Search
USPC ................... 606/79, 80, 81; 623/22.12, 22.22
See application file for complete search history.

(56) References Cited

U.S. PATENT DOCUMENTS

| | | | | |
|---|---|---|---|---|
| 5,376,092 A * | 12/1994 | Hein et al. | ...................... | 606/81 |
| 5,871,486 A * | 2/1999 | Huebner et al. | ............... | 606/305 |
| 6,764,490 B1 * | 7/2004 | Szabo | ............................. | 606/81 |
| 7,118,575 B2 * | 10/2006 | Wolford | .......................... | 606/80 |
| 2002/0107521 A1 * | 8/2002 | Petersen et al. | ................ | 606/85 |

* cited by examiner

*Primary Examiner* — Victor Nguyen
(74) *Attorney, Agent, or Firm* — Baker & Hostetler LLP

(57) ABSTRACT

Surgical cutting tool for manufacturing of a recess in a firm body tissue, in particular in a bone and/or in a cartilage, with a milling range rotatable around a central axis of rotation, with an outside lateral surface and an internal area substantially defined by the lateral surface and turned away from the worked on body tissue. The lateral surface is formed with at least two machining cutting edges, which proceed at the lateral surface from a machining center to a machining edge of the milling range and which are in particular spiral curved. Apertures are arranged adjacent to the cutting edges for the transport of the cutting splinters into the internal area, whereby the cutting edges are interrupted by means of recesses in such a way that the cutting edges are formed by individually cutting elements.

16 Claims, 8 Drawing Sheets

SURGICAL CUTTING TOOL

FIELD OF THE INVENTION

The invention relates to a surgical cutting tool for producing a recess in a solid body tissue, especially a bone and/or cartilage.

BACKGROUND OF THE INVENTION

Surgical cutting tools are known, for example as described in EP 1 227 762 B1. They are associated with the disadvantage in that in some cases the machined recesses produce faster and greater material removal in the edge region than in the central rotary centre, the so-called pole region.

SUMMARY OF THE INVENTION

It is an object of the present invention to provide a surgical cutting tool that makes it possible to work quickly and safely and to maintain a predetermined milling shape.

The present invention is a surgical cutting tool for producing a recess in a solid body tissue, in particular a bone and/or cartilage, said tool comprising a milling region that can be rotated about a central rotational axis, an outer lateral surface of the milling region, and an inner region which is essentially defined by the lateral surface and faces away from the body tissue to be machined. The lateral surface is embodied as a milling head with at least two chip-removing cutting edges which on the lateral surface extend from a rotary centre to a rotary edge of the milling region, and are in particular spiral-shaped. Apertures are arranged adjacent to the cutting edges, for the transport of the chips to the inner region, wherein the cutting edges are interrupted by means of recesses that are embodied as cutting elements acting in an individually cutting manner, and at least two stop surfaces arranged adjacently, which on the lateral surface essentially extend parallel in the longitudinal direction of the surface. These stop surfaces on the lateral surface extend essentially parallel to the cutting edge and delimit penetration of the cutting edges in the body tissue in a cutting direction arranged across the longitudinal direction of the surface in relation to the penetration depth into the tissue. A first stop surface, which delimits a first penetration of the cutting edge into the tissue, comprises a height difference relative to a cutting edge tip, which height difference starting from the region in the rotary centre remains essentially constant or decreases to a small extent towards the region on the rotary edge. A second stop surface, which delimits penetration of the cutting edge into the tissue, which penetration follows on from the first penetration, in relation to the cutting edge tip comprises a height difference which starting from the region in the rotary centre decreases towards the region on the rotary edge.

The stop surfaces prevent the cutting edge from penetrating too deeply into the tissue. By means of the first stop surface the cutting edge penetrating into the depth is decelerated. Further deceleration then takes place by the second stop surface. The height of the stop surfaces decreases from the central rotary centre of the milling head to the edge of the milling head. Thus the depth of cutting of the cutting edge is reduced towards the edge. The deepest cut thus at first takes place in the rotary centre, and the desired milling shape is not distorted.

The object is further met by a surgical cutting tool for producing a recess in a solid body tissue, in particular a bone and/or cartilage, which comprises a milling region that can be rotated about a central rotational axis, an outer lateral surface of the milling region, and an inner region which is essentially defined by the lateral surface and faces away from the body tissue to be machined. The lateral surface is embodied as a milling head with at least two chip-removing cutting edges which extend on the lateral surface from a rotary centre to a rotary edge of the milling region, and are in particular spiral-shaped. Apertures are arranged adjacent to the cutting edges, for the transport of the chips to the inner region, wherein the cutting edges are interrupted by means of recesses such that they are embodied as cutting elements acting in an individually cutting manner, with a groove-shaped recess that extends spirally on the lateral surface and on the lateral surface in the region of the recesses in the cutting edges breaches the cutting edges such that the groove-shaped recess forms a practically continuously-aligned continuation of the recesses in the cutting edges, and in this manner a chip-breaking division of the cutting edges into cutting edge elements arises, wherein the length of the cutting elements starting from the rotary centre decreases towards the rotary edge.

The groove-shaped recess supports the milling head during advance into the tissue, thus providing a type of guidance. At the same time, tissue material that has been removed by milling by the recess is transported to the next opening from where it moves through the opening to the inside of the milling head. At the same time the recesses in the cutting edges have a chip-breaking effect. The length of the cutting elements formed by the recesses decreases from the rotary centre to the rotary edge. In this manner, in turn, a reduction in the removal from the rotary centre to the rotary edge is achieved and the certainty of shape during milling is increased.

The object is further met by a surgical cutting tool for producing a recess in a solid body tissue, in particular a bone and/or cartilage, which comprises a milling region that can be rotated about a central rotational axis, an outer lateral surface of the milling region, and an inner region which is essentially defined by the lateral surface and faces away from the body tissue to be machined, wherein the lateral surface is embodied as a milling head with at least two chip-removing cutting edges which extend on the lateral surface from a rotary centre to a rotary edge of the milling region, and are in particular spiral-shaped. Apertures are arranged adjacent to the cutting edges, for the transport of the chips to the inner region, wherein the cutting edges are interrupted by means of recesses such that they are embodied as cutting elements acting in an individually cutting manner, wherein the openings are continuously open essentially parallel to the cutting edges and end in the region of the rotary centre and in the region of the rotary edge.

The large openings make it possible to quickly and reliably remove the chips. Furthermore, the stability of the milling head is assured by a mounting support at the rotary centre and at the rotary edge.

It is advantageous if the cutting edges, when viewed in cross section, in each case comprise a rake angle alpha that is formed between the lateral surface and a cutting surface that faces away from the workpiece, with said rake angle increasing from the cutting edge in the region of the rotary centre to the cutting edge in the region on the rotary edge.

It is advantageous if the cutting edges, when viewed in cross section, in each case comprise a clearance angle gamma that is formed between the lateral surface and the cutting surface that faces the workpiece, with said clearance angle decreasing from the cutting edge in the region of the rotary centre to the cutting edge in the region on the rotary edge.

It is advantageous if the clearance angle gamma decreases incrementally and/or continuously depending on the distance from the rotary centre.

It is advantageous if the stop surfaces comprise a concave cross-section.

It is advantageous if the cutting surface of the workpiece, which cutting surface faces the workpiece, remains essentially constant along the entire cutting edge.

It is advantageous if the cross section of the groove-shaped recess is rounded or angular.

It is advantageous if the cutting edge is divided by recesses into approximately 5 to 8 cutting elements.

It is advantageous if the milling region is designed so as to be hemispherical or triangular or planar or tapered or conical or mushroom-shaped.

It is advantageous if the milling region comprises recesses in the side of the lateral surface in order to place the milling region in tissue regions that are difficult to access, wherein the envelope of the milling region remains practically unchanged compared to the tool comprising a solid design.

It is advantageous if the milling region comprises approximately 2 to 8, preferably 6, cutting edges that are preferably arranged equidistantly around the lateral surface.

It is advantageous if the milling region is manufactured from a highly heat-resistant metal, in particular a Cr—Co alloy, and/or from a highly heat-resistant plastic, in particular PEEK (polyether ether ketone), and/or from a ceramic material, particular comprising zirconium oxide.

As presented, the invention relates to a surgical cutting tool for producing a recess in a cartilage tissue and/or bone tissue for a prosthetic joint, in particular in a hip joint bone for a cup prosthesis comprising an essentially hemispherical lateral surface and a hollow inner region defined by the aforesaid, wherein on the lateral surface a cutting device extending towards the equator of the lateral surface, which cutting device comprises at least one cutting element with a cutting surface facing the workpiece and a cutting surface facing away from the workpiece, as well as a cooperating opening in the lateral surface for the transport of the chips into the hollow inner region, wherein for rotation on the symmetry axis that forms the rotational axis advantageously a lateral surface through the hollow inner region is provided.

However, such cutting tools are associated with a disadvantage in that, as a result of the greater cutting speed, the hemispherical tool head always has increased material removal towards the edge or towards the equator. Consequently, the geometric shape of the recesses deviates from the design required for the prosthesis. This results in an inaccurate fit between the recess and the cup prosthesis accommodated therein, so that the patient needs to undergo an operation at relatively short intervals in order to have a new prosthesis inserted.

It is the object of the present invention, among other things, to create a surgical cutting tool to form a recess in a cartilage and/or bone tissue, in particular in a hip joint bone for a cup prosthesis, by means of which cutting tool a recess of a geometric form that is as accurate as possible can be manufactured.

The surgical cutting tool comprises in particular a clearance angle γ of the cutting element, which clearance angle γ is formed between the lateral surface and the cutting surface facing the workpiece, and which clearance angle γ decreases from the pole of the lateral surface in the direction of the equator of the lateral surface.

As a result of the decrease in the clearance angle γ, material removal towards the edge or equator of the hemisphere is reduced so that the geometric shape of the recess almost exactly corresponds to the shape of the hemispherical cutting tool. Because of the exact nature of the hemispherical recess the accuracy of fit between the cup prosthesis and the indentation is improved so that the service life of the prosthesis used is prolonged. Consequently the intervals between the operations in which the patient has a new prosthesis fitted are prolonged.

Furthermore, because of the reduction in the clearance angle towards the edge of the cutting tool, the tendency of the cutting tool according to the invention not providing a true cut is reduced when compared to conventional cutting tools, because the maximum cutting power of the cutting tool according to the invention is arranged so as to be closer to the pole of the lateral surface. This results in the cutting tool, when compared to conventional cutting tools, with corresponding advance in the direction of the rotational axis, being self-centering during the cutting process.

In an improved embodiment, manufacture of the cutting tool is particularly simple, in particular when the cutting edge comprises a multitude of cutting elements.

With an improved embodiment the cutting behaviour of the cutting tool can be improved because the clearance angle γ is continuously adjusted depending on the distance from the rotational axis.

An improved embodiment provides an advantage in that the cutting tool comprises a significantly more uniform cutting characteristic in the entire cutting region because the maximum advancement depth hc of the cutting device is constant in the entire cutting circumference so that the cutting properties of the cutting tool are optimised. The maximum. advancement depth $hc = 2r\pi \tan \gamma$, which shows that there is an indirect proportionality between the distance of the cutting device to the rotational axis and $\tan \gamma$, wherein the clearance angle γ is between 0° and 90°, i.e. when the distance between the cutting device and the rotational axis increases, the clearance angle γ decreases.

By means of an improved embodiment the cutting volume of the material can be adjusted according to the radius, wherein the clearance angle γ of the cutting element and the rake angle α of the cutting element are advantageously matched with regard to the material to be machined.

Furthermore, the improved embodiment provides an advantage in that the effective cutting length of the cutting device is increased, wherein during chip-removal, apart from shear forces in the direction of rotation, an additional component of shear forces towards the outside occurs, and consequently material removal is possible with less force being expended.

An improved embodiment provides an advantage in that the cutting tool during the cutting process is stabilised as a result of several cutting devices being in simultaneous engagement so that the cutting tool hardly deviates from the desired rotational axis. Furthermore, in this way vibrations of the cutting tool are reduced so that the surface quality of the recess produced is improved.

In an improved embodiment advantageous stabilisation and vibration reduction occurs, wherein the manufacture of the cutting tool is economical. Furthermore, at least three cutting devices are effective in the same circumference in order to ensure the stability of the construction.

As shown in the above description, multiple variations and modifications to the initial design can be made without leaving the scope of the invention. For example, the cutting device extending from the pole of the lateral surface to the equator of the lateral surface can also comprise a multitude of independent cutting elements. Furthermore, a cutting tool according to the invention can be firmly clamped into place wherein the workpiece is rotated. Moreover, the lateral surface of the cutting tool can have a shape that does not correspond to a complete hemisphere but that is similar to a hemisphere or corresponds to part of a hemisphere, which part does not extend as far as the equator. Furthermore, the guide element can also comprise circular elements arranged on the lateral surface, or a multitude of individual segments.

Further characteristics and advantages of the invention are stated in the description below in which exemplary embodiments of the subject of the invention are explained in more detail in conjunction with the drawings.

BRIEF DESCRIPTION OF THE DRAWINGS

FIG. 5b illustrates a top view of the cutting tool of FIG. 5a.

DETAILED DESCRIPTION OF THE PREFERRED EMBODIMENTS

Figure 1:
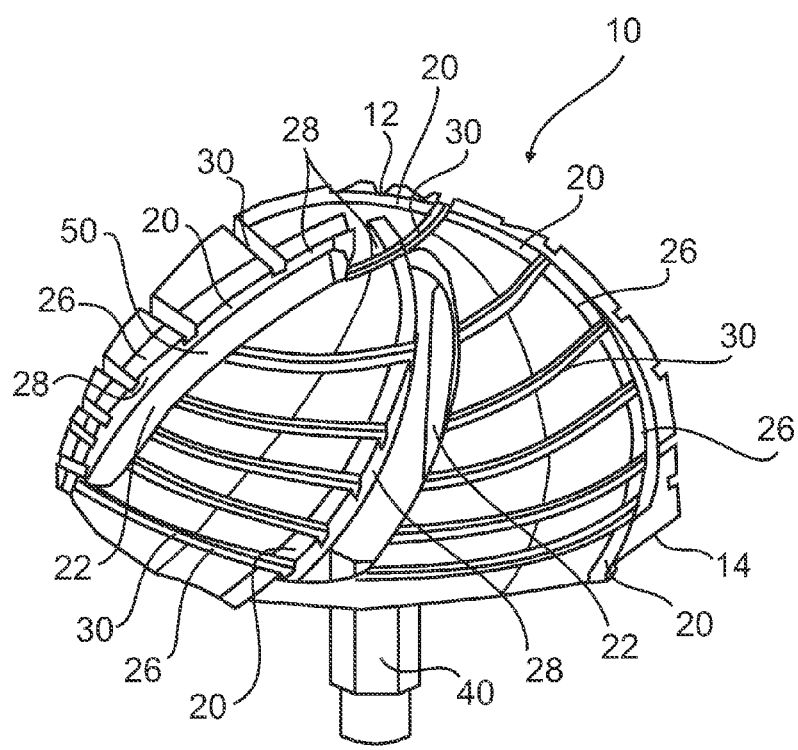
FIG. 1 illustrates a cutting tool.
Figure 2A:
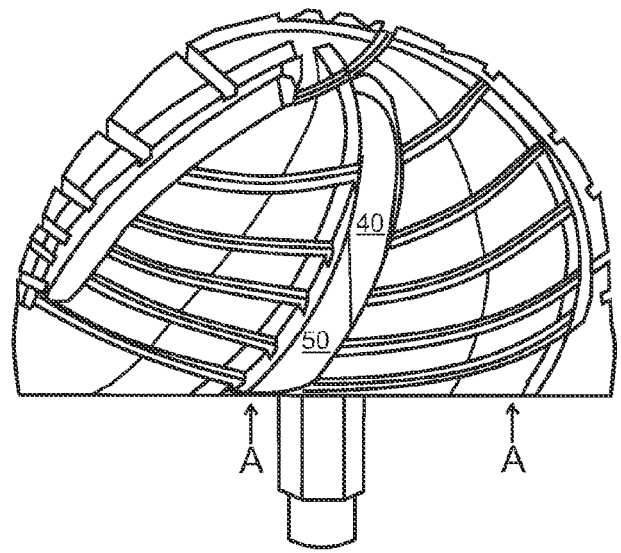
FIG. 2a illustrates a lateral view of a cutting tool.
Figure 2B:
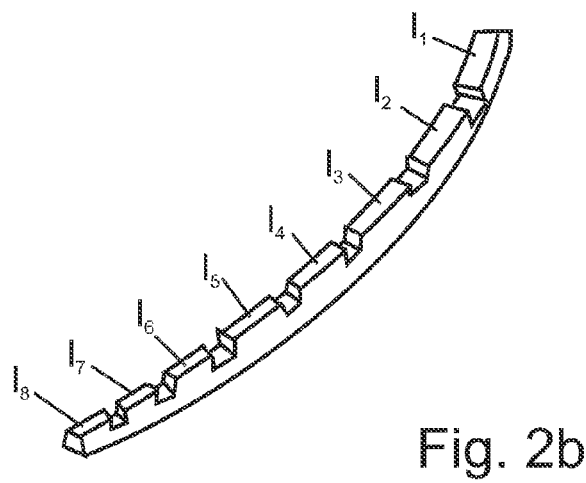
FIG. 2b illustrates a cutting edge with recesses and cutting elements.
Figure 3A:
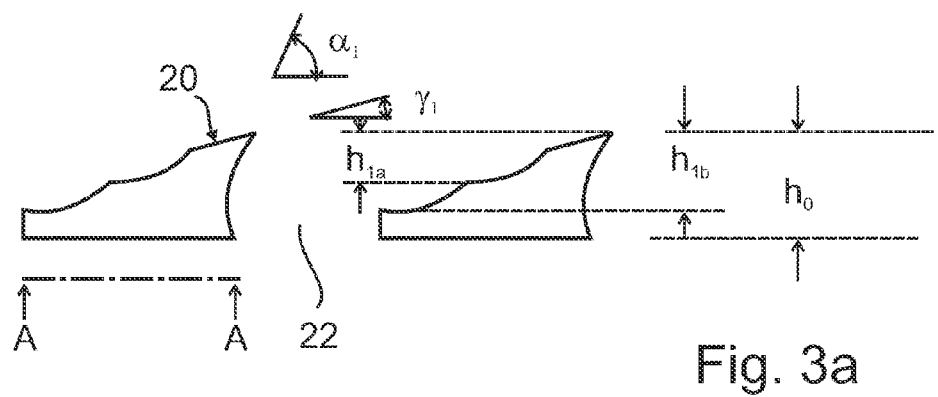
FIG. 3a is a view taken along a cross section AA of a lateral surface from FIG. 2a in the pole region.
Figure 3B:
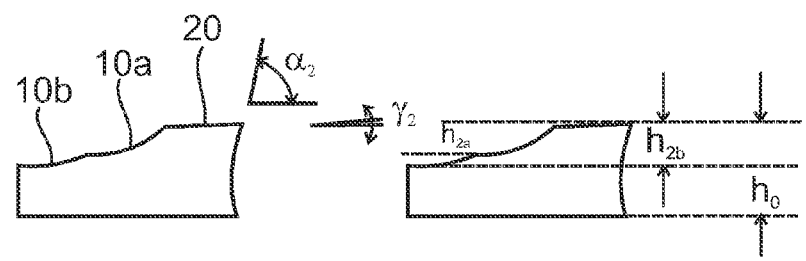
FIG. 3b is a view taken along a cross section AA of a lateral surface from FIG. 2a in the equator region.
Figure 4:
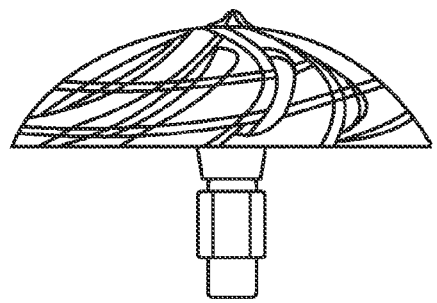
FIG. 4 illustrates a lateral view of a cutting tool.
Figure 5A:
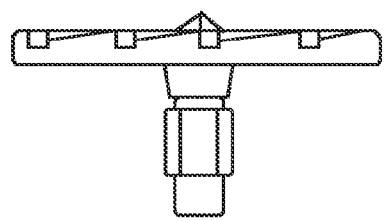
FIG. 5a illustrates a side view of another embodiment of the cutting tool.
Figure 5B:
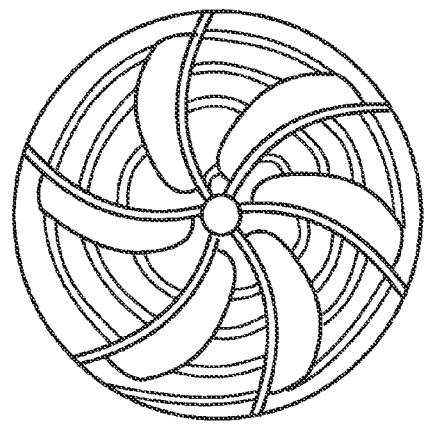
Figure 6:
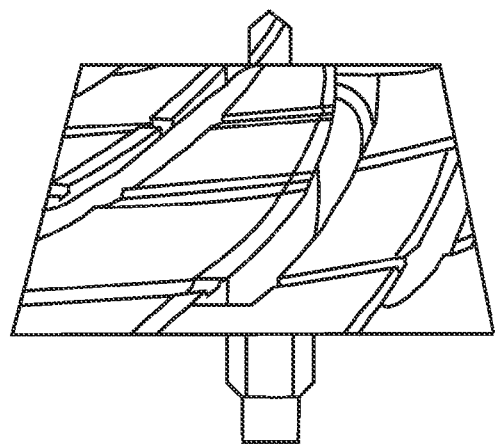
FIG. 6 illustrates a cutting tool.
Figure 7A:
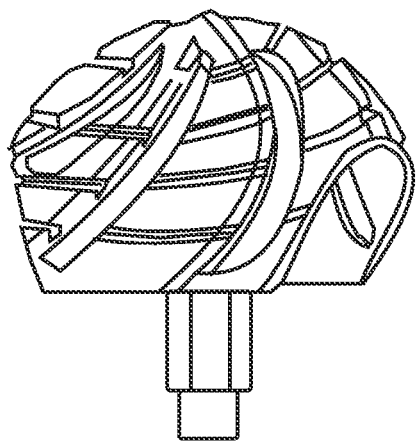
FIG. 7a illustrates a cutting tool with a lateral recess.
Figure 7B:
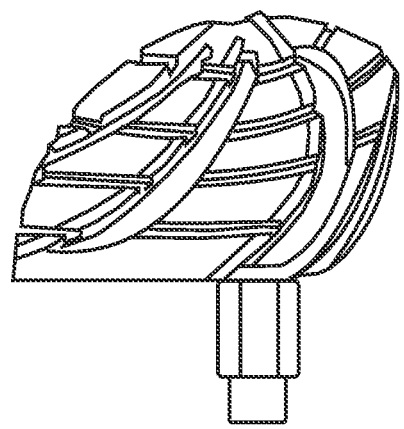
FIG. 7b illustrates a cutting tool with a lateral recess.

FIG. 1 shows a surgical cutting tool with a hemispherical lateral surface 10 and an inner region 50 delimited by the aforesaid, which cutting tool can be rotated on a central axis by means of a bearing shaft 40. In this arrangement rotation takes place clockwise when viewed from the direction of the bearing shaft. From the rotary centre, namely from pole 12, cutting edges extend on cutting devices 20, which are divided into individual cutting elements by means of recesses 30 penetrating the cutting edge. The length of the cutting elements decreases from the pole 12 to the equator 14. The cutting devices comprise a first cutting surface 28 that faces away from the workpiece, and a second cutting surface 26 that faces the workpiece.

The indentation 30 extends in the form of a spiral over the entire lateral surface from the pole 12 to the equator 14.

The newly placed groove-shaped recess, which extends in a spiral shape from the pole 12 to the equator 14 and can be angular or round, leads through the cutting edges. This results in individual chip-breaking cutting elements that arise where the groove intersects the cutting edges. This translates into improved cutting characteristics of the cutting device. Because, as a result of the design of the cutting elements, the overall length of the cutting surface of the cutting edges is reduced to 70% of the length of the cutting edge, the danger of the device getting stuck is considerably reduced. At the same time the cutting characteristics are not reduced, and a perfect cartilage recess or bone recess is produced.

Overall, the cutting edge is preferably divided into approximately 5 to 8 cutting elements.

The chip-breaking devices are produced towards the equator 14 by means of grooves with reduced spacing to each other. In this manner the length of the cutting elements steadily decreases from the pole 12 to the equator 14. This in turn results in the cutting force being reduced towards the equator 14, and the accuracy of guidance of the cutting device being increased.

In addition, the spiral-shaped groove itself acts as a guide element because the cartilage/bone that in the chip-breaking region is not removed by the cutting element enters the spiral. This results in stabilisation of the milling device until the following cutting element removes the aforesaid. The groove furthermore serves as an auxiliary to promote advance, similar to a corkscrew, as long as pressure is exerted on the milling device.

The cutting device is held together at the rotary centre (h1b) and at the rotary edge (h2b).

The chip thickness depends on the difference between the cutting edge and the adjacent lateral surface, wherein the opening for carrying through the chips is arranged between the lateral surface and the cutting edge. The work height between the tip of the cutting edge and the end of the second lateral surface (10b) preferably decreases continuously from the cutting edge region in the rotary centre (h1b) to the cutting edge region on the rotary edge (h2b). This considerably improves the accuracy of guiding the milling device.

In each case between two cutting edges the lateral surface of the milling device is formed by two different surfaces: a first cutting surface 28 formed so as to face away from the cutting edge, and a second cutting surface 26 extending to the opening between the aforesaid and the adjacent cutting edge. The surfaces act to stop advancement. As a result of a differently increasing space when compared to the absolute milling shape, the surfaces of the milling device make it possible to achieve greater aggressiveness.

The difference between the second surface and the surface of the following cutting edge, as a result of decreasing space from the equator, results in more aggressiveness in the pole region and thus in improved directional accuracy.

The width of the cutting edge surface is the same along the entire length from the pole 12 to the equator 14.

The openings in the lateral surfaces, which openings are located in front of each cutting edge, extend at a distance of approximately 2 to 7 mm from the rotary centre ("pole") to a distance of approximately 0.5 to 3 mm to the rotary edge ("equator").

By means of the invention a recess is machined in the body's own hard tissue, in particular in bone or cartilage.

This recess can, in particular, be hemispherical and can then be used as a replacement region, for example for hip joint prostheses.

In one embodiment of a surgical cutting tool it comprises a hemispherical tool head 10 in the form of a hemispherical lateral surface 10 and a hollow inner region 50 delimited by the aforesaid. On the hemispherical lateral surface 10, cutting devices 20 are arranged that extend from the pole 12 of the lateral surface 10 to the equator 14 of the lateral surface 10, wherein the cutting devices 20 are uniformly distributed over the lateral surface 10 and are spiral-shaped so that the cutting devices 20 depict the form of a propeller.

For the purpose of moving the chips into the hollow inner region 50, there are openings 22 in the lateral surface 10 between the cutting devices 20 and the guide element 30. During the cutting process the cutting tool shown rotates, wherein each cutting device 20 comprises a multitude of notches 24 that serve as chip-breaking devices so that the chips, produced by the cutting devices 20, of a workpiece (not shown) are transported through the openings 22 into the hollow inner region 50, wherein the length of the notches 24 increases from the pole 12 to the equator 14. Furthermore, a bearing shaft 40 that extends through the hollow inner region 50 is attached to the lateral surface 10, in particular to the pole 12 that forms both the rotary axis and the symmetry axis of the cutting tool. Part of the bearing shaft 40 can be seen through openings 22 in the hollow inner region 50.

The diagram shows a lateral view of the embodiment of the cutting tool, wherein in particular the shape of the hemispherical lateral surface 10 is evident.

For example, a clearance angle $\gamma$ is formed between the lateral surface 10 and the cutting surface 26 of the cutting element or of the cutting device 20, which cutting surface 26 faces the workpiece. On the other hand a rake angle forms between the lateral surface 10 and the cutting surface 28 of the cutting element or of the cutting device 20, which cutting surface 28 faces away from the workpiece.

Moreover, the clearance angle $\gamma$ and the rake angle $\alpha$ of the cutting element 20 in the region of the equator 14 of the lateral surface 10 are shown. In this arrangement the clearance angle can be greater or smaller, wherein chip removal of the cutting device 20 from the pole 12 of the lateral surface 10 decreases in the direction of the equator 14 of the lateral surface 10 as a result of the decrease in the clearance angle $\gamma$.

When the rake angle $\alpha$ increases, the chipping volume of the material can adjust according to the radius. Thus the rake angle $\alpha$ of the cutting device 20, which rake angle $\alpha$ is formed between the lateral surface 10 and the cutting surface 28 of the cutting element or of the cutting device 20, which cutting surface 28 faces away from the workpiece, advantageously increases from the pole 12 of the lateral surface 10 in the direction of the equator 14 of the lateral surface 10.

In a graphic representation the cutting performance relative to the diameter of cutting tools can be shown, wherein the x-axis denotes the diameter of cutting tools, while the y-axis denotes the cutting performance of cutting tools. A curve 70 shows the progression of the cutting performance of a cutting tool according to the invention over the diameter, whereas a curve 60 shows the progression of the cutting performance of a diameter, wherein the dashed line indicates the cutting performance of 100%. The intersection of the curves 60, 70 with the x-axis indicates the pole 12 of the cutting tools, wherein the cutting speed in the pole 12 of the cutting tools is zero.

The cutting performance of the cutting tool according to the invention is greater than that of a conventional cutting tool because the surface below curve 70 is greater. Furthermore, as a result of the decrease in the clearance angle $\gamma$ of the cutting device 20 towards the edge or pole 12 of the cutting tool, the tendency of the cutting tool according to the invention to not run "true" is reduced when compared to conventional cutting tools arranged closer to the pole 12 of the lateral surface 10. This results in the cutting tool according to the invention acting so as to self-center during the cutting process if there is corresponding advance in the direction of the rotational axis.

In an advantageous embodiment three cutting devices can be distributed over the lateral surface, wherein the individual cutting devices comprise cutting elements that are arranged between concentric circles of the lateral surface and that are curved.

Figure 8:
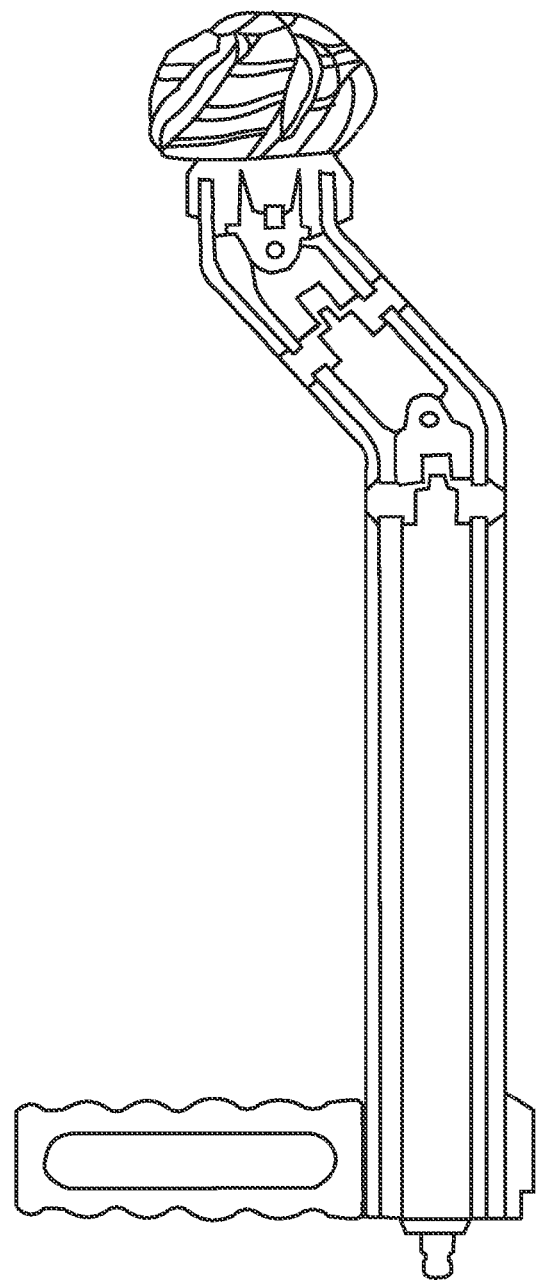
FIG. 8 illustrates a cutting tool with an adapter for attachment to a drive tool.
Figure 9:
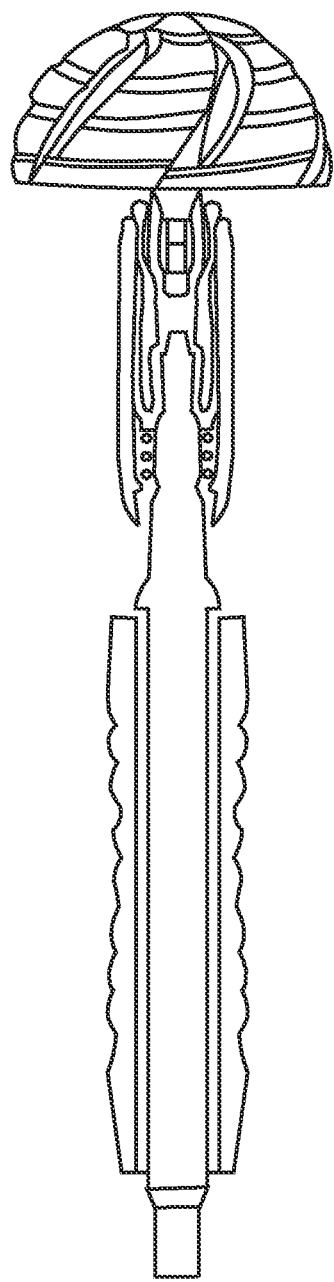
FIG. 9 illustrates a cutting tool with an adapter for attachment to another kind of drive tool.

FIGS. 8 and 9 show a cutting tool with an adapter for attachment to a drive tool, for example a power tool or a hand tool.

The invention claimed is:

1. A surgical cutting tool for forming a recess in a body tissue, comprising:

a milling area on the surgical cutting tool that is rotatable around a central axis of rotation and has an outside lateral surface and an internal area which is substantially defined by the outside lateral surface and facing away from the machined body tissue, the outside lateral surface having at least two curved machining cutting edges which are formed thereon to provide a milling head and which proceed at the outside lateral surface from a machining center to a machining edge of the milling area, and apertures formed in the surgical cutting tool arranged adjacent to the cutting edges and configured to transport cutting splinters from the machined body tissue into the internal area, whereby the cutting edges are interrupted by recesses formed in the cutting edges to form individual cutting elements, wherein the outside lateral surfaces between two cutting edges comprise at least two stop surfaces which are arranged substantially parallel and adjacent to the cutting edges, and the stop surfaces are configured to limit the penetration of the cutting edges into the body tissue in relation to the penetration depth into the tissue, and wherein a first stop surface of the at least two stop surfaces limiting a first penetration of the cutting edge into the tissue has a first differential height in relation to a tip of the cutting edge, wherein the first differential height is essentially constant or slightly declining between a region of the rotational center and a circumferential region of the surgical cutting tool, and a second stop surface of the at least two stop surfaces extends to the opening of the second cutting edge and limits the penetration following the first penetration of the cutting edge into the tissue, wherein the second stop surface has a second differential height in relation to the tip of the cutting edge, which second differential height decreases from the region of the rotational center toward the circumferential region.

2. The surgical cutting tool of claim 1, comprising a helical groove formed on the outside lateral surface, wherein the helical groove breaks through the cutting edges at the lateral surface in the area of the recessions of the cutting edges in such a way that the groove forms a substantially aligned continuation of the recessions within the cutting edges and a chip breaking partition of the cutting edges into cutting elements is formed, whereas the lengths of the cutting elements decrease from the machining center to the machining edge.

3. The surgical cutting tool of claim 2, wherein the cross section of the groove is rounded or angular.

4. The surgical cutting tool of claim 1, wherein the apertures are formed essentially parallel to the cutting edges and continuously open and end in the area of the rotational center and in the area of the circumferential edge.

5. The surgical cutting tool of claim 1, wherein each of the cutting edges subtends, when observed in cross section, a cutting angle alpha, which is formed between the lateral surface and a cutting surface which is facing away from the workpiece, the cutting angle alpha increasing from the cutting edge at the area of the rotational center towards the cutting edge within the area of the circumferential edge.

6. The surgical cutting tool of claim 5, wherein the milling area is made of a Cr—Co alloy.

7. The surgical cutting tool of claim 1, wherein the cutting edges provide, when observed in cross section, a clearance angle gamma, which is formed between the lateral surface and a cutting surface facing the workpiece, and which clearance angle decreases from the cutting edge within the area of the rotational center toward the cutting edge within the area of the circumferential edge.

8. The surgical cutting tool of claim 7, wherein the clearance angle gamma decreases continuously in relation to the distance from the rotational center.

9. The surgical cutting tool of claim 1, wherein the stop surfaces have a concave cross section.

10. The surgical cutting tool of claim 1, wherein the cutting edge which is facing the workpiece is essentially constant over the entire cutting edge.

11. The surgical cutting tool of claim 1, wherein the cutting edge is separated by recesses into approximately 5 to 8 cutting elements.

12. The surgical cutting tool of claim 1, wherein the milling area is hemispherical or formed like an triangle or flat or conically or mushroom-shaped.

13. The surgical cutting tool of claim 1, wherein the milling area has recesses in the side of the lateral surface that are configured to permit access to difficult accessible areas of the body tissue and an envelope of the milling area remains essentially unchanged compared to a full working tool.

14. The surgical cutting tool of claim 1, wherein the milling area comprises about 2 to 8 cutting edges which are arranged equidistantly over the lateral surface.

15. The surgical cutting tool of claim 1, wherein the milling area is made of a high-temperature resistant metal.

16. The surgical cutting tool of claim 1, wherein the milling area comprises 6 cutting edges arranged equidistantly over the lateral surface.

* * * * *